US011549874B2

(12) United States Patent
He et al.

(10) Patent No.: US 11,549,874 B2
(45) Date of Patent: Jan. 10, 2023

(54) METHOD AND APPARATUS FOR USING A GAS DENSITY SENSOR TO CONTROL GAS MIXTURE COMPOSITION

(71) Applicant: Air Products and Chemicals, Inc., Allentown, PA (US)

(72) Inventors: Liang He, Allentown, PA (US); Ranajit Ghosh, Macungie, PA (US); Donald James Bowe, Pennsburg, PA (US); Reed Jacob Hendershot, Orefield, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 192 days.

(21) Appl. No.: 17/151,928

(22) Filed: Jan. 19, 2021

(65) Prior Publication Data
US 2021/0140865 A1 May 13, 2021

Related U.S. Application Data

(62) Division of application No. 16/100,073, filed on Aug. 9, 2018, now Pat. No. 10,928,287.

(51) Int. Cl.
*G01N 9/36* (2006.01)
*G01N 9/26* (2006.01)
(Continued)

(52) U.S. Cl.
CPC ........... *G01N 9/36* (2013.01); *B01F 35/2134* (2022.01); *G01G 17/04* (2013.01); *G01N 9/266* (2013.01); *G05D 11/137* (2013.01)

(58) Field of Classification Search
CPC .......... G01N 9/00; G01N 9/002; G01N 9/266; G01N 9/36; G01N 2291/02818;
(Continued)

(56) References Cited

U.S. PATENT DOCUMENTS 4,734,609 A * 3/1988 Jasmine ................. G01N 9/002
310/317
4,845,976 A 7/1989 Johnson et al.
(Continued)

FOREIGN PATENT DOCUMENTS

DE   10 2014 115 566 A1   5/2015
WO   WO 2017102222 A1   6/2017

OTHER PUBLICATIONS

Kramer, A., et al.; "High-Precision Density Sensor for Concentration Monitoring of Binary Gas Mixtures"; Procedia Engineering; 47; 2012; pp. 44-47; Elsevier.
(Continued)

*Primary Examiner* — Andre J Allen
(74) *Attorney, Agent, or Firm* — Amy Carr-Trexler

(57) ABSTRACT

An apparatus for controlling blending of a gas mixture containing known components, including first, second, and third control valves for controlling the flow of first, second, and third components, respectively, a first gas density sensor to measure the density of a first mixture of the first and second components, a second gas density sensor to measure the density of a second mixture of the first mixture and the third component, and a controller to determine based on data from the first and second gas density sensors the relative compositions of the first, second, and third components in the second mixture, and to control the first, second, and third control valves to obtain a desired relative composition of the first, second, and third components in the second mixture.

8 Claims, 2 Drawing Sheets

(51) Int. Cl.
*G05D 11/13* (2006.01)
*G01G 17/04* (2006.01)
*B01F 35/21* (2022.01)

(58) Field of Classification Search
CPC ........... G01N 2009/006; G01N 29/036; G01N 33/0004; G01N 21/35; G01N 2291/021; G01N 9/26; G01N 33/225; G01N 2021/0385; G01N 27/75; G01N 21/7703; G01N 21/7746; G01N 21/80; G01N 21/81; G01N 29/022; G01N 2021/772; G01N 27/048; G01N 21/4133; G01N 2291/02809; G01N 11/16; G01N 2291/0427; G01N 25/005; G01N 25/18; G01N 33/22; G01N 9/10; G01N 1/2035; G01N 2001/205; G01N 2021/0314; G01N 2021/0396; G01N 2021/3181; G01N 2033/4975; G01N 2201/0833; G01N 2291/0256; G01N 2291/02881; G01N 2291/2697; G01N 29/2481; G01N 29/30; G01N 29/4472; G01N 33/0006; G01N 33/0059; G01N 33/007; G01N 33/4972; G01N 9/34; G01N 1/2202; G01N 1/2247; G01N 2001/2223; G01N 2001/2264; G01N 2001/227; G01N 2033/0068; G01N 21/3504; G01N 21/43; G01N 2291/02836; G01N 29/024; G01N 9/24; G01N 1/4055; G01N 2001/4061; G01N 21/783; G01N 2203/0226; G01N 2203/028; G01N 2291/014; G01N 2291/0217; G01N 2291/022; G01N 2291/103; G01N 27/18; G01N 27/4175; G01N 29/02; G01N 29/222; G01N 29/348; G01N 29/46; G01N 3/04; G01N 33/0016; G01N 33/0036; G01N 33/0067; G01N 33/497; G01N 5/04; G01N 13/00; G01N 13/04; G01N 15/0205; G01N 15/0606; G01N 2011/0006; G01N 2011/0013; G01N 2011/002; G01N 2015/0046; G01N 2015/0693; G01N 2021/0364; G01N 2021/1731; G01N 2021/3185; G01N 2021/451; G01N 2021/6482; G01N 2021/651; G01N 2030/8854; G01N 21/00; G01N 21/31; G01N 21/314; G01N 21/3554; G01N 21/49; G01N 21/5907; G01N 21/64; G01N 21/65; G01N 2201/1211; G01N 2201/1214; G01N 2291/012; G01N 2291/024; G01N 2291/02845; G01N 2291/02863; G01N 2291/02872; G01N 2291/0426; G01N 25/66; G01N 27/00; G01N 27/12; G01N 27/4067; G01N 27/407; G01N 29/302; G01N 29/22; G01N 29/326; G01N 29/42; G01N 29/4436; G01N 30/86; G01N 30/8675; G01N 33/00; G01N 33/0009; G01N 33/0027; G01N 33/0031; G01N 33/0032; G01N 33/0037; G01N 33/004; G01N 33/0047; G01N 33/0062; G01N 33/0063; G01N 33/0065; G01N 33/0073; G01N 33/02; G01N 33/2823; G01N 35/00871; G01N 5/02; G01N 5/025; G05D 11/137; G05D 7/0635; G05D 7/0629; G05D 7/06; G05D 16/2006; G05D 16/0616; G05D 16/2093; G05D 23/1919; G05D 11/02; G05D 11/135; G05D 11/139; G05D 27/02

See application file for complete search history.

(56) References Cited

U.S. PATENT DOCUMENTS

| | | | |
|---|---|---|---|
| 5,159,843 | A | 11/1992 | Shakkottai et al. |
| 6,334,356 | B1 * | 1/2002 | Kita .................. G01N 29/036 73/54.01 |
| 6,997,037 | B2 | 2/2006 | Thurston |
| 7,184,895 | B2 | 2/2007 | Chetay et al. |
| 9,239,271 | B2 | 1/2016 | Downie et al. |
| 9,255,870 | B2 | 2/2016 | Downie et al. |
| 9,448,090 | B2 | 9/2016 | Downie |
| 9,459,191 | B2 | 10/2016 | Downie |
| 9,581,297 | B2 | 2/2017 | Downie et al. |
| 9,690,304 | B2 | 6/2017 | Downie |
| 9,870,007 | B2 | 1/2018 | Downie et al. |
| 9,927,402 | B2 | 3/2018 | Kramer et al. |
| 2002/0095262 | A1 | 7/2002 | Chetay et al. |
| 2016/0290849 | A1 | 10/2016 | Badarlis et al. |
| 2016/0313160 | A1 | 10/2016 | Ueberschlag et al. |

OTHER PUBLICATIONS

Lotters, J.C., et al.; "Real-Time Composition Determination of Gas Mixtures"; Department of Research & Development, Netherlands; MESA+Institute of Nanotechnology; 2014.

Sell, J.K., et al.; "Simultaneous Measurement of Density and Viscosity in Gases with a Quartz Tuning Fork Resonator by Tracking of the Series Resonance Frequency"; Procedia Engineering; 25; 2011; pp. 1297-1300; Elsevier.

* cited by examiner

METHOD AND APPARATUS FOR USING A GAS DENSITY SENSOR TO CONTROL GAS MIXTURE COMPOSITION

CROSS REFERENCE TO RELATED APPLICATIONS

This application is a divisional of, and claims the priority of, U.S. patent application Ser. No. 16/100,073 filed Aug. 9, 2018, which is incorporated by reference herein in its entirety.

BACKGROUND

The present invention relates to an apparatus and method of measuring a gas mixture composition, including mixtures having more than two components.

A thermal conductivity based sensor can be used as a binary gas mixture analyzer. For example, because hydrogen has a larger thermal conductivity than nitrogen, a thermal conductivity analyzer can be used to measure the composition of nitrogen-hydrogen gas mixture.

Infrared or laser measurement techniques, or gas chromatography, can be used to measure gas composition of gas mixture that contains more than two components. But these methods are expensive and most of time a pump and/or sampling system is needed to get the gas sample for analysis. And, the equipment usually needs a large floor area or special protection and maintenance.

Sometimes, to measure the composition of gas mixture that has more than two components, various technologies can be combined into one analysis unit to measure concentration of each component.

Long-time reliability, expensive equipment, frequent maintenance, and safety considerations are the main issues in the measurement of composition of gas mixture. Also, if the pump or sampling system is needed, usually the response time is relatively long and cannot meet the requirements in some applications.

Gas density sensors are used to measure composition of binary gas mixture. In one example, a gas density sensor to continuously measure the gas density of natural gas to predict the potential heating value of the specific natural gas flow, but not to determine the composition.

At present, use of a gas density sensor to measure gas composition is limited to binary gas mixture, and not to measure the composition of a gas mixture that contains more than two components. For example, density, pressure, and temperature sensors are currently being used in the heat treating industry to measure the furnace atmosphere (N2-H2 mixture) in sintering furnaces. However, this application, using the gas density sensor to measure the composition of the already-mixed gas mixtures, can only be possible for binary gas mixture.

SUMMARY

Systems and methods are described herein for measure, and controlling, the composition of a gaseous mixture having three or more components, using sensor configured to measure density, and preferably also pressure and temperature. By measuring pressure, temperature, and gas density together, the molecular weight of gas can be accurately calculated. (This calculation is also possible by measuring density only, if a reasonable estimate of temperature and pressure can be made.) If the components of a binary, tertiary, or beyond gas mixture are known, and in particular if the molecular weight of each of the components is known, then the gas composition (i.e., the relative proportion of each component) can be measured with by a system using such a sensor. Because gas density sensors are inexpensive and can be constructed to be reliable, this type of sensor is advantageous over present methods of measuring gas mixture composition, particularly in gas mixtures with more than two components.

BRIEF DESCRIPTION OF THE DRAWINGS

The present invention will hereinafter be described in conjunction with the appended figures wherein like numerals denote like elements.

DETAILED DESCRIPTION

A system and method are described herein for using one or more gas density sensors to measure the composition of a gas mixture made from component gases each with a known or knowable molecular weight. Preferably, the temperature and the pressure of each gas mixture are also measured at the same time as the gas density, to improve accuracy of the molecular weight calculation. Using this system and method, the composition of gas mixtures having two, three, or more components can be measured accurately and inexpensively.

Figure 1:
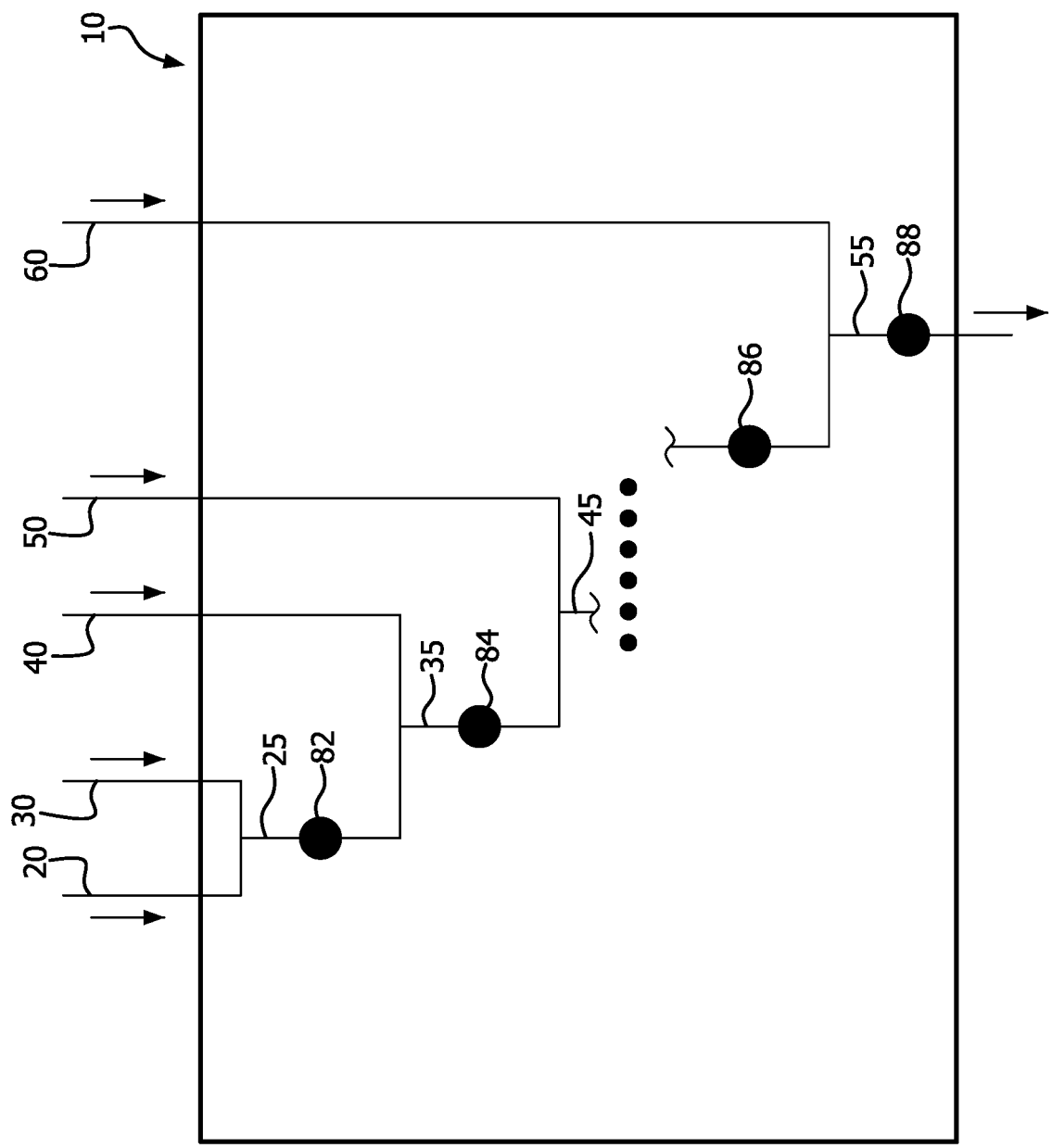
FIG. 1 is a schematic view of a system for determining the composition of a multi-component mixture using a plurality of gas density sensors to serially determine binary mixture density (and thus composition) as each successive component is added, wherein the number of gas density sensors is one less than the number of mixture components to be detected.

An embodiment of a gas composition measurement system 10 for measuring a mixture of n known gaseous components (or at least n components of known molecular weight) is shown in FIG. 1. A supply line supplies each component to the system 10. In the depicted embodiment, a supply line 20 carries a Component-1, a supply line 30 carries a Component-2, a supply line 40 carries a Component-3, a supply line 50 carries a Component-4, and for illustrative purposes, a supply line 60 carries a Component-n.

Component-1 and Component-2 are mixed at a junction 25 to form a first gas mixture, and a first density sensor 82 measures the density of the first gas mixture. Component-3 and the first gas mixture are mixed at a junction 35 to form a second gas mixture, and a second gas density sensor 84 measures the density of the second gas mixture. Component-4 and the second gas mixture are mixed at a junction 45 to form a third gas mixture, and a third gas density sensor (not shown) measures the density of the third gas mixture. Eventually, an n−2 gas mixture, whose density is measured by an n−2 gas density sensor 86, is mixed with Component-n at a junction 55, and an n−1 gas density sensor 88 measures the density of the n−1 gas mixture.

Each of the sensors 82, 84, 86, and 88 can be a combination sensor that determines not only gas density but also temperature and pressure of the gas. Pressure and temperature can be used to accurately calculate molecular weight, and can also be used to apply correction factors to the density measurement to improve accuracy, particular at high pressure or for certain gases that may deviate from the ideal gas law. With the measured pressure, temperature, and gas density, the molecular weight of a mixture can be calculated, and from that the relative amount of each of the components that went into the mixture (i.e., gas composition) can be calculated.

Information from each of the sensors 82, 84, 86, and 88 is supplied to a processor, which maybe a PLC or controller or computer or any kind of data-processor that can collect the signal from the sensors 82, 84, 86, and 88 and run mathematical calculations to determine the composition of each gas mixture. By processing the calculations in series, the processor repeatedly solves one equation for one unknown, in sequence, to determine the compositions of the intermediate and final mixtures. Thus, for a gas mixture containing n components, n−1 sensors are needed and n−1 molecular weight calculations are performed.

The system will show the calculated composition of each gas mixture on a screen or will record it to a file, or will make the information available through another data access method. For example, each gas density sensor may send its measurement results to a central computer (or data logger machine) through wired or wireless communication and the central computer (or data logger machine) then runs calculations and shows the gas composition information that is needed for process control or monitoring.

Figure 2:
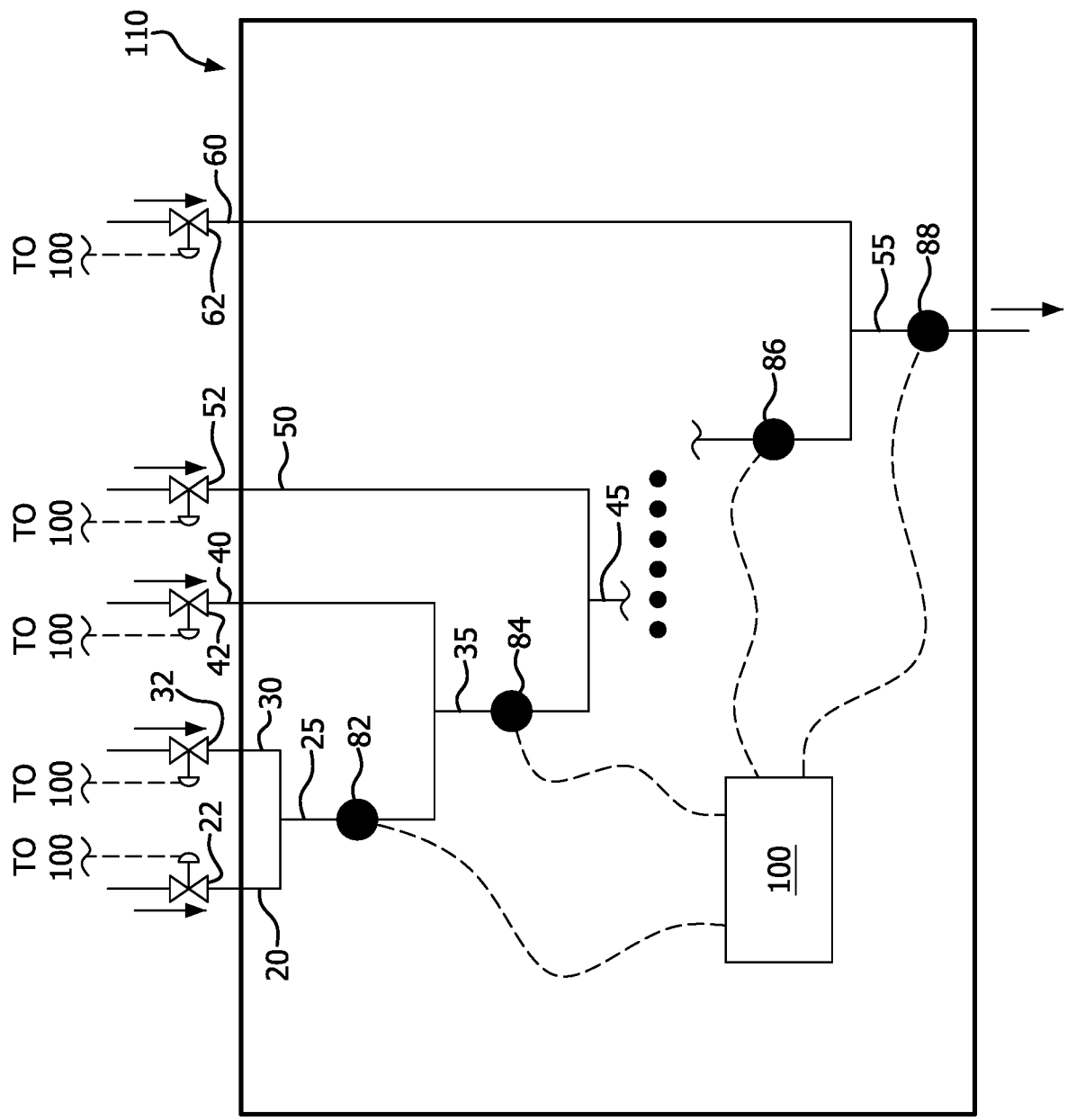
FIG. 2 is a schematic view of a system as in FIG. 1 further including a controller to receive data from the gas density sensors and determine intermediate and final mixture compositions, and control valves on each input line to control the mixture compositions.

In a further embodiment as shown in FIG. 2, a gas composition measurement and control system 110 is shown for measuring a mixture of n known gaseous components (or at least n components of known molecular weight), and then controlling the composition of that mixture. In addition to the components in the system 10 of FIG. 1, the system 110 also includes a central controller 100 as well as control valves 22, 32, 42, 52, and 62, on the supply lines 20, 30, 40, 50, and 60 for Component-1, Component-2, Component-3, Component-4, and Component-n, respectively. The controller 100 receives data from each of the sensors 82, 84, 86, and 88, computes the composition of the intermediate and final mixtures, compares one or more of the calculated mixture compositions to a target mixture composition, and then iteratively adjusts one or more of the control valves 22, 32, 42, 52, and 62 to achieve the target mixture composition.

While the principles of the invention have been described above in connection with preferred embodiments, it is to be clearly understood that this description is made only by way of example and not as a limitation of the scope of the invention.

The invention claimed is:

1. An apparatus for controlling the blending of a gas mixture containing known components, comprising:
   a first control valve for controlling the flow of a first component;
   a second control valve for controlling the flow of a second component;
   a first gas density sensor configured and arranged to measure the density of a first mixture made by combining the first component and the second component;
   a third control valve for controlling the flow of a third component;
   a second gas density sensor configured and arranged to measure the density of a second mixture made by combining the first mixture with the third component; and
   a controller programmed to determine based on data from the first gas density sensor the relative compositions of the first component and the second component in the first mixture, and to determine based on the data from the second gas density sensor the relative compositions of the first mixture and the third component in the second mixture, and thus to determine the relative compositions of the first component, the second component, and the third component in the second mixture; and
   the controller being further programmed to control the first control valve, the second control valve, and the third control valve to obtain a desired relative composition of the first component, the second component, and the third component in the second mixture.

2. The apparatus of claim 1, further comprising:
   a fourth control valve for controlling the flow of a fourth component;
   a third gas density sensor configured and arranged to measure the density of a third mixture made by combining the second mixture with the fourth component; and
   the controller being further programmed to determined based on data from the third gas density sensor the relative compositions of the second mixture and fourth component in the third mixture, and thus to determine the relative compositions of the first component, the second component, the third component, and the fourth component in the third mixture; and
   the controller being further programmed to control the fourth control valve to obtain a desired relative composition of the first component, the second component, the third component, and the fourth component in the third mixture.

3. The apparatus of claim 1, wherein the first component, the second component, and the third component each have a corresponding known molecular weight.

4. The apparatus of claim 1, further comprising:
   a first temperature sensor configured and arranged to measure the temperature of the first mixture and a first pressure sensor configured and arranged to measure the pressure of the first mixture; and
   a second temperature sensor configured and arranged to measure the temperature of the second mixture and a second pressure sensor configured and arranged to measure the pressure of the second mixture;
   wherein the controller is further programmed to take into account data from the first temperature sensor and the first pressure sensor in determining the relative compositions the first component and the second component in the first gas mixture; and
   wherein the controller is further programmed to take into account data from the second temperature sensor and the second pressure sensor in determining the relative compositions of the first mixture and the third component in the second mixture, and thus the relative compositions of the first component, the second component, and the third component in the second mixture.

5. A method for controlling the blending of a gas mixture containing know components, comprising:
   measuring the density of a first mixture made by combining a first component and a second component;
   measuring the density of a second mixture made by combining the first mixture with a third component;
   calculating based on the measured density of the first mixture the relative compositions of the first component and the second component in the first mixture, and calculating based on the measured density of the second mixture the relative compositions of the first mixture and the third component in the second mixture, and thus the relative compositions of the first component, the second component, and the third component in the second mixture; and controlling a flow of the first component, a flow of the second component, and a flow of the third component to obtain a desired relative composition of the first component, the second component, and the third component in the second mixture.

6. The method of claim 5, further comprising:

measuring the density of a third mixture made by combining the second mixture and a fourth component;

calculating based on the measured density of the third mixture the relative compositions of the second mixture and fourth component in the third mixture, and thus the relative compositions of the first component, the second component, the third component, and the fourth component in the third mixture; and controlling the flow of the first component, the flow of the second component, the flow of the third component, and a flow of a fourth component to obtain a desired relative composition of the first component, the second component, the third component, and the fourth component in the third mixture.

7. The method of claim 5, wherein the first component, the second component, and the third component each have a corresponding known molecular weight.

8. The method of claim 5, further comprising:

measuring the temperature of the first mixture;

measuring the pressure of the first mixture;

measuring the temperature of the second mixture;

measuring the pressure of the second mixture; and calculating based on the measured density, temperature, and pressure of the first mixture the relative compositions of the first component and the second component in the first mixture, and calculating based on the measured density, temperature, and pressure of the second mixture the relative compositions of the first mixture and the third component in the second mixture, and thus the relative compositions of the first component, the second component, and the third component in the second mixture.

* * * * *